United States Patent [19]

Kathawala

[11] 4,246,259

[45] Jan. 20, 1981

[54] HIGHER ALKYL DIARYL SULFONIUM SALTS

[75] Inventor: Faizulla G. Kathawala, West Orange, N.J.

[73] Assignee: Sandoz, Inc., E. Hanover, N.J.

[21] Appl. No.: 10,015

[22] Filed: Feb. 7, 1979

[51] Int. Cl.³ .................... A61K 31/69; A61K 31/095
[52] U.S. Cl. .................................... 424/185; 424/335; 568/18; 568/74
[58] Field of Search ............................. 424/185, 335; 260/607 B

[56] References Cited

U.S. PATENT DOCUMENTS

| | | | |
|---|---|---|---|
| 2,193,963 | 3/1940 | Harris | 260/607 B |
| 2,800,747 | 7/1957 | Pitt | 260/607 B |
| 3,534,105 | 10/1970 | Distler et al. | 260/607 B |

Primary Examiner—Frederick E. Waddell
Attorney, Agent, or Firm—Gerald D. Sharkin; Richard E. Vila; Frederick H. Weinfeldt

[57] ABSTRACT

Higher alkyl diaryl sulfonium salts, e.g., octadecyldiphenylsulfonium tetrafluoroborate, are useful as anti-obesity agents.

14 Claims, No Drawings

HIGHER ALKYL DIARYL SULFONIUM SALTS

This invention relates to higher alkyl diarylsulfonium salts useful as anti-obesity agents, and more particularly to pharmaceutical compositions containing such compounds, as well as to the pharmaceutical use of such compounds.

The compounds involved in this invention may be conveniently represented by the formula I:

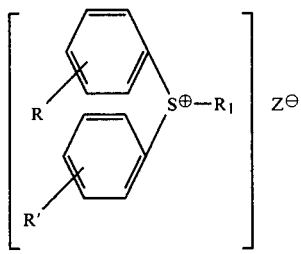

wherein
- each of R and R', is independently, hydrogen, halo of atomic weight of from 18 to 80, i.e. fluoro, chloro or bromo, alkyl of 1 to 4 carbon atoms, e.g., methyl, or alkoxy of 1 to 4 carbon atoms, e.g., methoxy;
- $R_1$ is alkyl of 10 to 24 carbon atoms; preferably from 14 to 20 carbon atoms; and
- $Z^\ominus$ is an anion forming a pharmaceutically acceptable non-toxic salt of the corresponding cation.

$R_1$ may be branched or unbranched, alkyl, but is preferably unbranched.

A preferred method (process a) of preparing compounds of the formula I involves reacting a compound of the formula II:

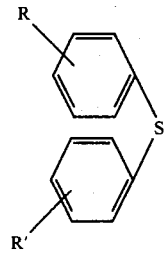

wherein R and R' are as above defined, with a compound of the formula III:

wherein $R_1$ is as above defined and X is bromo or iodo, in a solvent which is not detrimental to the reaction, in the presence of a salt of the formula IV:

wherein Z is as above defined (for $Z^-$), and M is a metal forming with X a salt MX which is either per se insoluble or relatively less soluble than the compound IV in the solvent.

Process (a) is carried out under essentially anhydrous conditions at moderate temperatures, e.g. from 15° C. to 40° C., in a suitable solvent which is preferably also a polar solvent, e.g. nitromethane. The reactants II and III are conveniently mixed in the solvent and the salt of the formula IV may be added thereto exercising suitable caution as may be required such as shielding from light. The reaction is also preferably carried out under an inert atmosphere, eg. dry nitrogen. An excess of the alkylhalide of the formula III is preferably employed and in most cases is highly desirable in order to increase the yield of the desired products. Illustrative of various MZ salts include the salts of noble metals of which silver represents a preferred metal. Other such metals include mercury. Representative anions ($Z^\ominus$) forming such salts include the tetrafluoroborate, trifluoromethylsulfonate and perchlorate ions. Other anions which may be represented by Z include the alkyl and phenyl sulfonates, eg. methanesulfonate, phenylsulfonate and p-toluenesulfonate. Examples of preferred salts of the formula IV include silver tetrafluoroborate and silver trifluoromethylsulfonate of which silver tetrafluoroborate is especially preferred. The resulting solvent insoluble salt, MX, is separated by known techniques and the desired product recovered from the solvent phase by applying conventional procedures to be selected in large part on the nature of the compound I being produced and the complexity of the remaining solvent reaction medium.

In other preparative procedures that may be defined as ion exchange reactions (generally herein designated process B), the compounds of the formula I may be converted into other salt forms.

For example, in a procedure herein designated process B-1, a compound of the formula I':

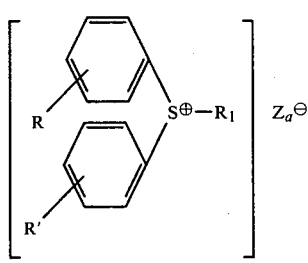

may be converted into a compound of the formula I":

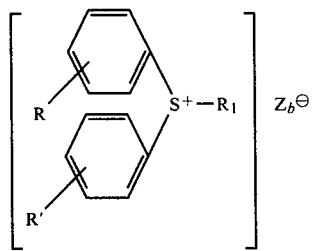

with R, R' and $R_1$ in formulae I' and I" being as above defined, and wherein $Z_b^\ominus$ is an anion forming a compound I having different solubility characteristics than formed with the anion $Z_a^\ominus$. Conversely, the anion $Z_a^\ominus$ is anion forming a compound I having different solubility characteristics than is formed with the anion $Z_b^\ominus$.

More particularly, the compounds of the formula I" may be prepared in process B-1 by heating a compound I' in aqueous cosolvent solution in the presence of an acid of the formula V:

H—Z$_b$ wherein Z$_b$ is as above defined, at temperatures typically of from about 55° C. to 120° C., preferably 65° C. to 100° C., desirably in the presence of a theoretical excess of the acid of the formula V, and separating the desired compound of the formula I″ from any unreacted starting material by taking advantage of its different solubility characteristics.

Preferred compounds of the formula I′ include those in which Z$_a^\ominus$ is the tetrafluoroborate ion. The aqueous cosolvent system comprises water and a sufficient amount of a water soluble organic solvent that the resulting aqueous cosolvent system is capable of dissolving the starting compound of the formula I′. Examples of such organic solvents include the lower alkanols, eg. methanol, ethanol and propanol, dimethylacetamide and dimethylformamide, particularly ethanol.

The initial isolation of the desired compound I″ in process B-1 may be effected by the application of various known procedures depending upon the solubility characteristics of the desired product and any remaining unreacted starting material, as would be apparent to those skilled in the art. For example, isolation may be readily effected in certain cases simply by lowering the temperature of the reaction to crystallize the desired product by taking advantage of its reduced solubility in the aqueous cosolvent system. In other cases the contents of the reaction mixture may be concentrated and redissolved in a solvent from which either the desired product or undesired starting material may be selectively crystallized. In still other cases the contents of the reaction mixture may be subjected to standard chromatography procedures or subjected to the action of ion exchange resins.

Another ion exchange procedure that is particularly convenient (and is herein designated process B-2) involves generally the reaction of a compound I‴.

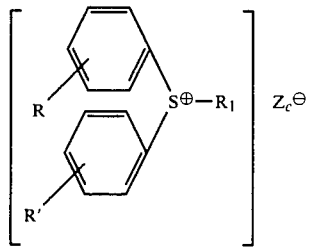

with a compound of the VI:

M$_a$Z$_d$     VI in an aqueous cosolvent solution to obtain a compound of the formula I$^{iv}$:

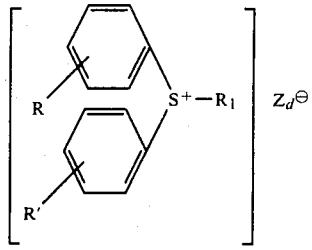

with R, R′ and R$_1$ in formulae I‴ and I$^{iv}$ being as above defined, and wherein M$_a$ is a metal cation forming with the anion Z$_c^\ominus$ a salt M$_a$Z$_c$ that is less soluble in the cosolvent solution than the compound I$^{iv}$, Z$_d$ is an anion forming with M$_a$ the cosolvent soluble salt VI that is more soluble than M$_a$Z$_c$ and Z$_c^\ominus$ is conversely an anion forming with M$_a$ the salt M$_a$Z$_c$.

The process B-2 is more particularly carried out in an aqueous solution at temperatures preferably in the range of 50° C. to 120° C., more preferably 80° C. to 100° C., preferably with a theoretical excess of the compound V. The aqueous cosolvent employed is composed similarly to that used in process B-1 with ethanol being commonly preferred as the organic component of such solvent system.

By way of illustration, a preferred embodiment of process B-2 involves the use of a compound I‴ in which Z$_c^\ominus$ is the tetrafluoroborate anion and M$_a$ is potassium whereby the insoluble potassium tetrafluoroborate is formed as a result of the reaction and may be separated from the reaction mixture by taking advantage of its insolubility in the aqueous cosolvent system. In such embodiment the desired compound of the formula I$^{iv}$ remains in the reaction system cosolvent and may be initially separated from any remaining undesired reactants and starting materials by employing conventional and well known procedures as in process B-1.

Other known ion exchange procedures such as those involving ion exchange resins may be employed, especially when representing a convenient method of separating desired products from reactants and starting materials in those procedures specifically detailed above, eg. processes B-1 and B-2. Typical ion exchange resins for such use are well known and are represented, for example, by the product obtainable under the trademark Dowex 1-X8. In effecting the initial solution of the desired products from ion exchange reactions such as processes B-1 and B-2 by chromatographic procedures both thin layer and column chromatography may of course be employed. Typical chromatography additives for such use are well known and are represented, for example, by silica gel and by the products obtainable under the trademarks Amberlite XAD-2 and Sephadex LH20.

Various other ways of employing ion exchange procedures, such as those specifically detailed above, will be recognized by those skilled in the art. For example, procedures such as processes B-1 and B-2, above, may be combined with process (a), above, as the final stages thereof, in order to obtain the ultimately desired compound I from an intermediary compound I without effecting an actual recovery of the latter.

Final recovery of the desired compound of the formula I from ion exchange procedures such as processes B-1 and B-2 may be also effected by conventional techniques such as crystallization, precipitation, vacuum distillation and the like.

Starting materials and reagents used in the above-described reactions, e.g., compounds II, III, IV and V are either known and obtained by methods described in the literature, or where not known, may be obtained by methods analogous to those described in the literature.

The compounds of Formula I are useful in inhibiting the passage of glucose into the blood in mammals, eg. as anti-obesity agents, as indicated by the glucose transport test in which male Wister rats are dosed orally with 0.3–80 mg./kg. body weight of the test compound after at least 20 hours of fasting. One hour after receiving the drug, each animal is sacrificed and the upper small intestine is removed and washed with glucose-saline. A 5 cm. section of the intestine is everted so that the mucosal surface is on the outside. One end of the segment is tied and the center of the sac so formed is filled with oxygen saturated Kreb's bicarbonate buffer. The other end is then closed to form a sac which is then incubated in 10 ml. of oxygen saturated bicarbonate buffer for 60 minutes at 37° C. Both the outside and inside solutions contain initially 0.3% of glucose. At the end of the incubation time, the glucose content of the outer (mucosal) and the inner (serosal) solution is determined using the standard Auto Analyzer procedure. Similar tests are run simultaneously with control animals receiving only the vehicle. The percent inhibition of glucose transport caused by the drug is calculated from the formula:

$$I = 100 - \left( \frac{S_t - M_t}{S_c - M_c} \times 100 \right),$$

wherein

I = percent inhibition, $S_t$ = glucose concentration (mg.%) of serosal fluid at the end of an experiment in the drug-treated animal, $S_c$ = glucose concentration (mg.%) of serosal fluid at the end of an experiment in the control animal, $M_t$ = glucose concentration (mg.%) of mucosal fluid at the end of an experiment in the drug-treated animal, and $M_c$ = glucose concentration (mg.%) of mucosal fluid at the end of an experiment in the control animal.

The precise dosage of the compound of Formula I to be employed depends upon several factors including the severity of the condition being treated and the particular compound employed. However, in general, satisfactory results, eg. in the treatment of obesity, are obtained when a compound of Formula I is administered orally at a daily dosage of 1–200 mg./kg. body weight, eg. a dosage of about 60–1500 mg. for most larger mammals. Usually, a small dosage is administered initially and the dosage is gradually increased until the optimal dosage for the host under treatment is determined. The daily dosage is usually divided into two to four equal portions, or placed in sustained release form. A typical unit dosage for larger mammals is 15–750 mg. for administration three times a day.

The compounds of Formula I may be formulated into conventional pharmaceutical compositions for oral administration.

The compounds may be combined with pharmaceutically acceptable carriers and other conventional pharmaceutical adjuvants and administered orally in the form of tablets, dispersible powders, granules, capsules, elixirs, suspensions and the like. The compositions may be prepared by conventional means and may contain one or more conventional adjuvants such as sweetening agents, other flavoring agents, coloring agents and preserving agents.

Tablets may contain the active ingredient in admixture with conventional excipients, i.e., inert diluents such as calcium carbonate, sodium carbonate, lactose, talc and sodium citrate, granulating and disintegrating agents, e.g., starch, gum tragacanth and alginic acid and also certain complex silicates, binding agents, e.g., starch, gelatin and acacia, and lubricating agents, e.g., magnesium stearate, stearic acid, talc and sodium lauryl sulfate. The tablets may be uncoated or coated by known techniques to delay disintegration and absorption in the gastrointestinal tract and thereby provide a sustained action over a longer period.

Capsules may contain a compound of Formula I alone but preferably admixed with an inert solid diluent, e.g., calcium carbonate, calcium phosphate, kaolin, lactose and high molecular weight polyethylene glycols.

Suspensions, syrups and elixirs may contain a compound of Formula I in admixture with any of the conventional excipients utilized for the preparation of such compositions i.e., suspending agents, e.g., methylcellulose, tragacanth and sodium alginate, wetting agents, e.g., lecithin, polyoxyethylene stearate and polyoxyethylene sorbitan monooleate, preservatives, e.g., ethyl p-hydroxybenzoate, and diluents, e.g., ethanol, propylene glycol and glycerin.

The preferred pharmaceutical compositions from the stand-point of ease of preparation and administration are solid compositions, particularly tablets and hard-filled capsules.

A typical dosage unit may contain 15 to 750 mg. of a compound of Formula I more typically 20 to 500 mg.

A representative formulation for administration orally three times a day prior to feeding in the treatment or lessening of obesity is a gelatin capsule prepared by conventional techniques to contain the following

| Ingredient | Weight (mg.) |
|---|---|
| Diphenyloctadecylsulfonium tetrafluoroborate | 75 |
| Lactose | 225 |

Salts (the values ($Z^\ominus$) judged to be of particular interest generally include the tetrafluoroborate, perchlorate, methanesulfonate, phenylsulfonate, p-toluenesulfonate, and 2-naphthylsulfonate.

The preferred compounds I are characterized by one or both of the following features: (a) those in which R and R' are the same and attached to the same position of the phenyl ring with which they are associated; and (b) those in which $R_1$ is chain alkyl of 14 to 20 carbon atoms.

The more preferred compounds are characterized by one or both of the following features: (a) those in which R and R' are both hydrogen; and (b) those in which $R_1$ is straight chain alkyl of 16 to 20 carbon atoms.

Among such more preferred compounds the especially preferred compounds I are those in which $R_1$ is straight alkyl of 18 carbon atoms, ie. n-octadecyl, eg. diphenyloctadecylsulfonium tetrafluoroborate.

In the following examples, which merely illustrate the invention, room temperature is 20° to 30° C., unless indicated otherwise.

EXAMPLE 1 n-octadecyldiphenylsulfonium tetrafluoroborate

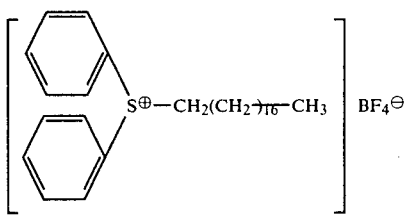

To a solution of 9.5 g. of diphenyl sulphide and 19.4 g. of octadecyl iodide in 100 ml. of methylene chloride and 75 ml. of nitromethane is added in small portions 10.0 g. of silvertetrafluoroborate. With exclusion of moisture and light, the reaction mixture is stirred at room temperature for 48 hrs. The reaction mixture is then filtered free of solids, the filtrate passed through a short layer of celite and evaporated i.v. to dryness. The oily residue is taken up in methylene chloride and purified by gel filtration over silica gel. Crystallization from ethanol gives the title compound, m.p. 69°–71° C.

EXAMPLE 2

Following the procedure of Example 1 using appropriate starting materials, the following additional compounds of the invention are prepared:

(a) n-tetradecyldiphenylsulfonium tetrafluoroborate (m.p. 58°–59° );

(b) n-hexadecyldiphenylsulfonium tetrafluoroborate;

(c) n-octadecyldiphenylsulfonium perchlorate;

(d) n-octadecyldiphenylsulfonium trifluoromethylsulfonate;

(e) n-octadecyldi(p-chlorophenyl)sulfonium tetrafluoroborate; and (f) n-hexadecyldi(p-methoxyphenyl)sulfonium tetrafluoroborate (as an oil).

EXAMPLE 3 n-octadecyldiphenylsulfonium p-toluene sulfonate

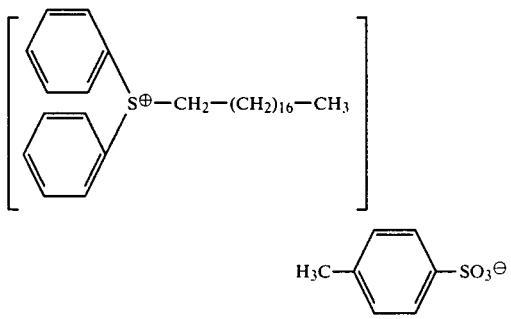

To a solution of 5.0 g diphenyl-n-octadecyl sulfonium tetrafluoroborate in 20 ml. of ethanol is added 20.0 g of potassiumtosylate dissolved in a mixture of 200 ml. ethanol and 10 ml. water. The reaction mixture is maintained at 80°–90° while being stirred vigorously for 2 hours. The reaction mixture is then cooled and evaporated i.v. to dryness. The residue is taken up in methylene chloride; the organic phase washed several times with water, dried over sodium sulphate, filtered and evaporated i.v. to dryness. The residue is chromatographed over silica gel three times using methylene chloride and increasing amounts of methanol to obtain n-octadecyldiphenylsulfonium p-toluenesulfonate.

EXAMPLE 4

Following the procedure of Example 3 the following additional compounds of the invention are prepared:

(a) n-octadecyldiphenylsulfonium methanesulfonate;

(b) n-octadecyldiphenylsulfonium phenylsulfonate; and (c) n-tetradecyldiphenylsulfonium p-toluenesulfonate.

What is claimed is:

1. The method of treating obesity in a mammal in need of such treatment comprising administering to a mammal an obesity-inhibiting amount of a compound of the formula:

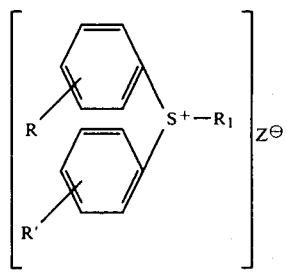

wherein

R and R' are independently hydrogen, fluoro, chloro, bromo, alkyl of 1 to 4 carbon atoms or alkoxy of 1 to 4 carbon atoms, $R_1$ is alkyl of 10 to 24 carbon atoms, and $Z^\ominus$ is an anion forming a pharmaceutically acceptable non-toxic salt of the corresponding cation.

2. The method of claim 1 in which $R_1$ is alkyl of 14 to 20 carbon atoms.

3. The method of claim 1 in which R and R' are each hydrogen.

4. The method of claim 1 in which $Z^\ominus$ is selected from the group consisting of the tetrafluoroborate, perchlorate, trifluoromethylsulfonate, methanesulfonate, p-toluenesulfonate and phenylsulfonate anions.

5. The method of claim 4 in which $R_1$ is straight chain alkyl of 14 to 20 carbon atoms.

6. The method of claim 2 in which $R_1$ is n-octadecyl.

7. The method of claim 5 in which $R_1$ is n-octadecyl.

8. The method of claim 7 in which each of R and R' is hydrogen.

9. The method of claim 8 in which the compound is n-octadecyldiphenylsulfonium tetrafluoroborate.

10. The method of claim 5 in which the compound is n-tetradecyldiphenylsulfonium tetrafluoroborate.

11. The method of claim 2 in which the compound is n-hexadecyl di(p-methoxyphenyl)sulfonium tetrafluoroborate.

12. The method of claim 4 in which $Z^\ominus$ of the compound is tetrafluoroborate.

13. The method of claim 8 in which the compound is n-octadecyldiphenylsulfonium p-toluenesulfonate.

14. The method of claim 1 in which the compound is administered in a daily amount of from 60 to 1500 milligrams.

* * * * *